US006341395B1

(12) United States Patent
Chao

(10) Patent No.: US 6,341,395 B1
(45) Date of Patent: Jan. 29, 2002

(54) VENTILATING BED CUSHION

(76) Inventor: Yu-Chao Chao, No. 73-1 Tsao Chung Lane, Lu-Kang Town, Chang-Hua Hsien (TW)

( * ) Notice: Subject to any disclaimer, the term of this patent is extended or adjusted under 35 U.S.C. 154(b) by 6 days.

(21) Appl. No.: 09/624,989

(22) Filed: Jul. 25, 2000

(51) Int. Cl.[7] .................................................. A61F 7/12
(52) U.S. Cl. ................................ 5/423; 5/726; 5/652.2
(58) Field of Search ........................... 5/423, 421, 726, 5/652.1, 652.2, 933; 290/180.1, 180.13, 180.14; 601/15, 18, 19, 84, 99, 115

(56) References Cited

U.S. PATENT DOCUMENTS 3,866,612 A * 2/1975 Buker .......................... 5/423

* cited by examiner

*Primary Examiner*—Lynne H. Browne
*Assistant Examiner*—Fredrick Conley
(74) *Attorney, Agent, or Firm*—Rosenberg, Klein & Lee

(57) ABSTRACT

A ventilating bed cushion includes a frame, a ventilating device, an air supplying device, an upper layer of air-permeable fabric and a lower layer of waterproof fabric. The ventilating device has a polished upper surface and a lower surface. The upper surface is formed with multiple vents. The ventilating device is formed with an inner air guide way for supplying a predetermined amount of air. Therefore, a specific portion of a patient's body lying on the bed cushion can be forcedly ventilated so as to avoid decubitus. In addition, the ventilating bed cushion is widely applicable and can be easily operated. In addition, it has a massaging effect and a low-cost simple structure.

3 Claims, 5 Drawing Sheets

VENTILATING BED CUSHION

BACKGROUND OF THE INVENTION

The present invention relates to a ventilating bed cushion, and more particularly to a ventilating bed cushion in which the ventilating device is movable to a desired position for forcedly ventilating a specific portion of a patient's body lying on the bed cushion so as to avoid decubitus. The air supplying device can also provide steaming treatment effect and massaging effect. The ventilating bed cushion has wide application range and can be easily operated. In addition, the ventilating bed cushion has simple structure and is manufactured at low cost.

FIG. 1 shows a conventional bed 90 including a hard bed board 91 and a soft bed cushion 92. with respect to physically defective users, especially those who need to live in a hospital or lie on the bed for a long term, such as a patient, a maimed person or an old-timer, a relative or a guardian must frequently turn the patient's body on the bed. However, in the case of hot weather or poor ventilation or insufficient turning, the patient often suffers decubitus on the back and additionally get hurt.

Therefore, it is necessary to provide an improved bed product which is manufactured at low cost and can be easily operated to avoid the above problem.

SUMMARY OF THE INVENTION

It is therefore a primary object of the present invention to provide a ventilating bed cushion which is able to avoid decubitus and has wide application range and can be easily operated.

It is a further object of the present invention to provide the above ventilating bed cushion which can also provide steaming treatment effect and massaging effect.

It is still a further object of the present invention to provide the above ventilating bed cushion which has simple structure and is manufactured at low cost.

The present invention can be best understood through the following description and accompanying drawings wherein:

DETAILED DESCRIPTION OF THE PREFERRED EMBODIMENTS

Figure 1:
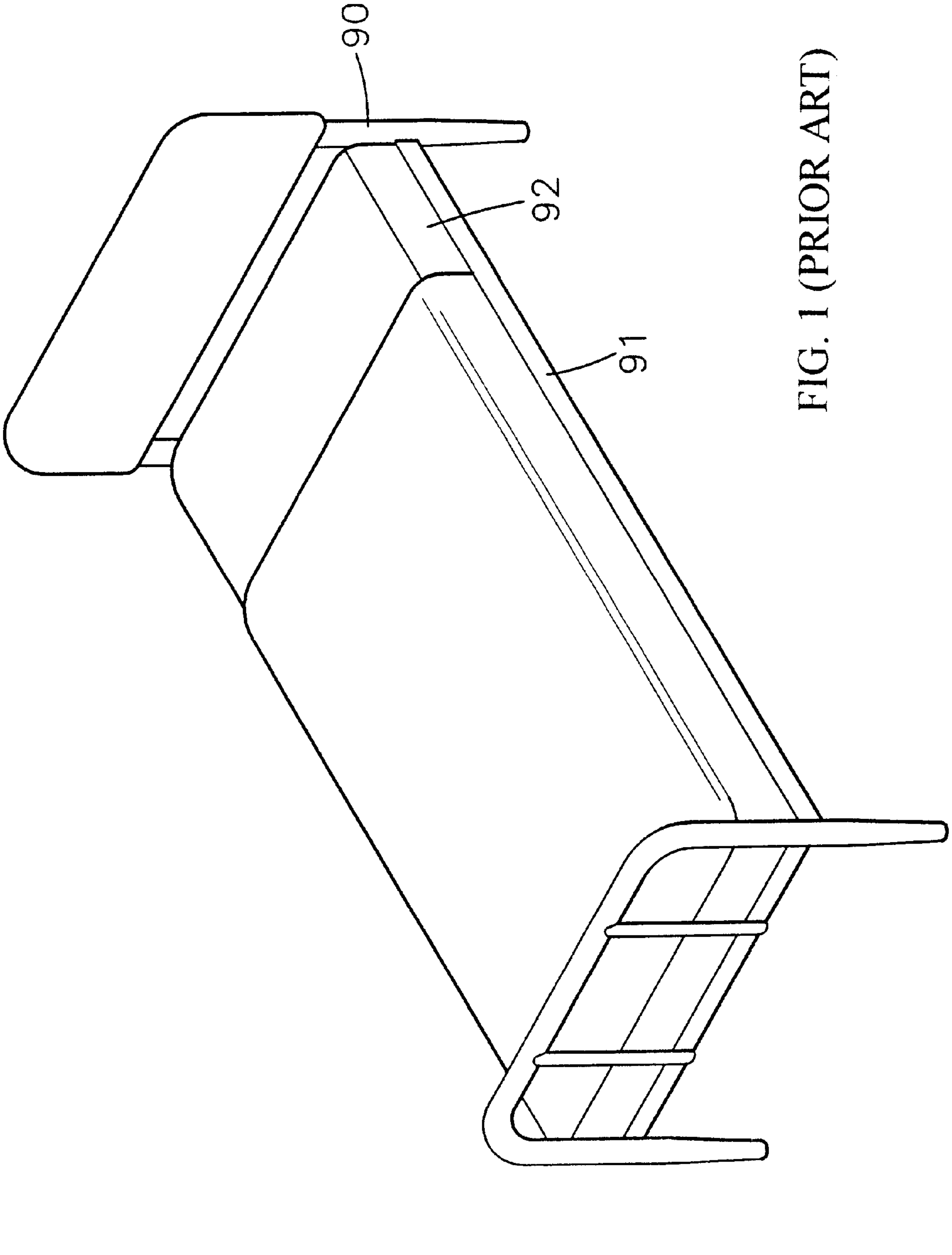
FIG. 1 (PRIOR ART)
FIG. 1 is a perspective view of a conventional bed.
Figure 2:
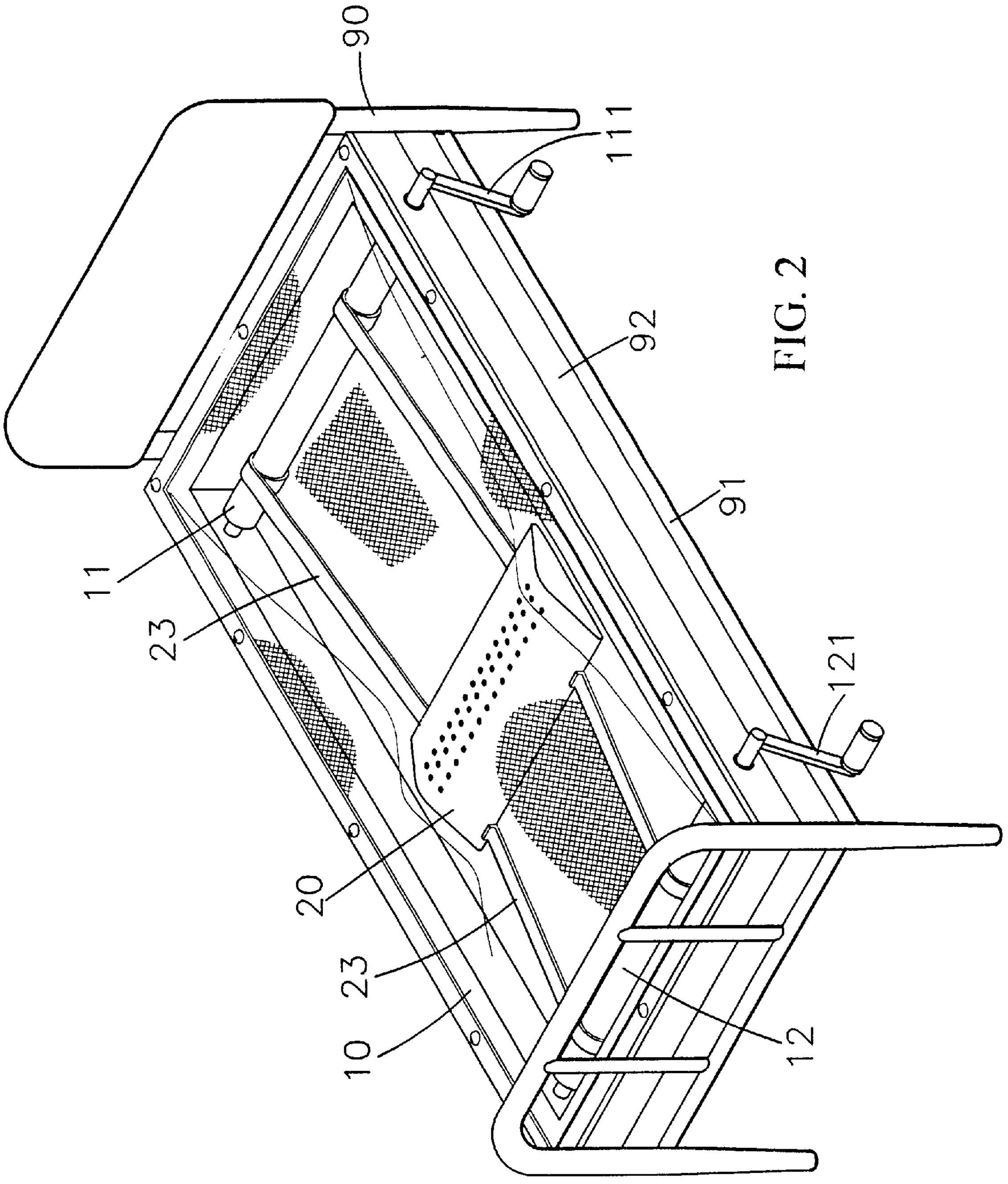
FIG. 2 is a perspective view of the present invention.
Figure 3:
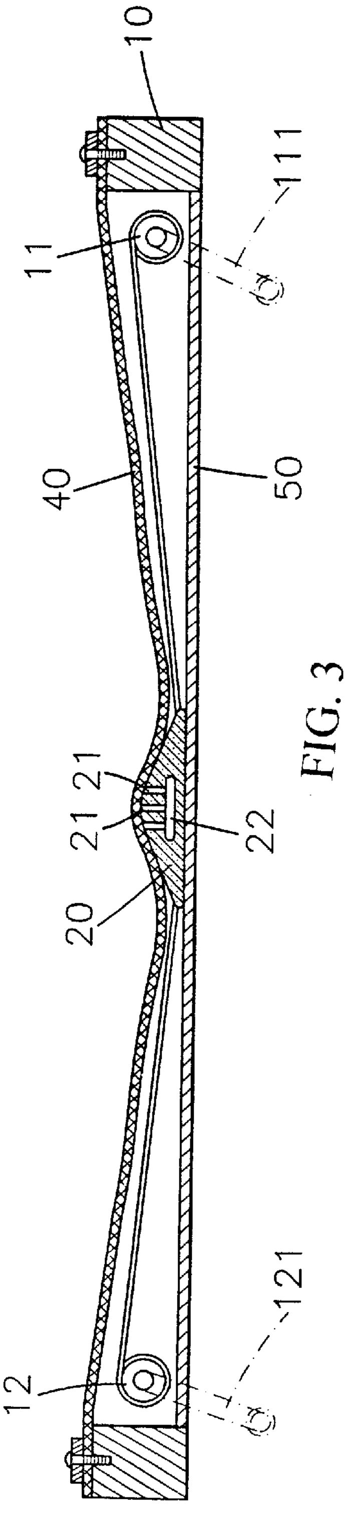
FIG. 3 is a sectional of the present invention.
Figure 4:
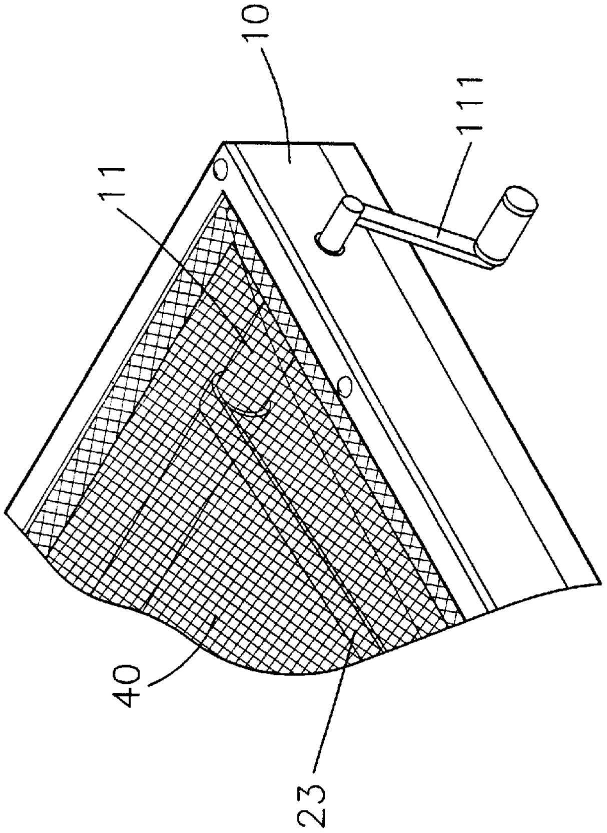
FIG. 4 is an enlarged perspective view of a part of the present invention.
Figure 5:
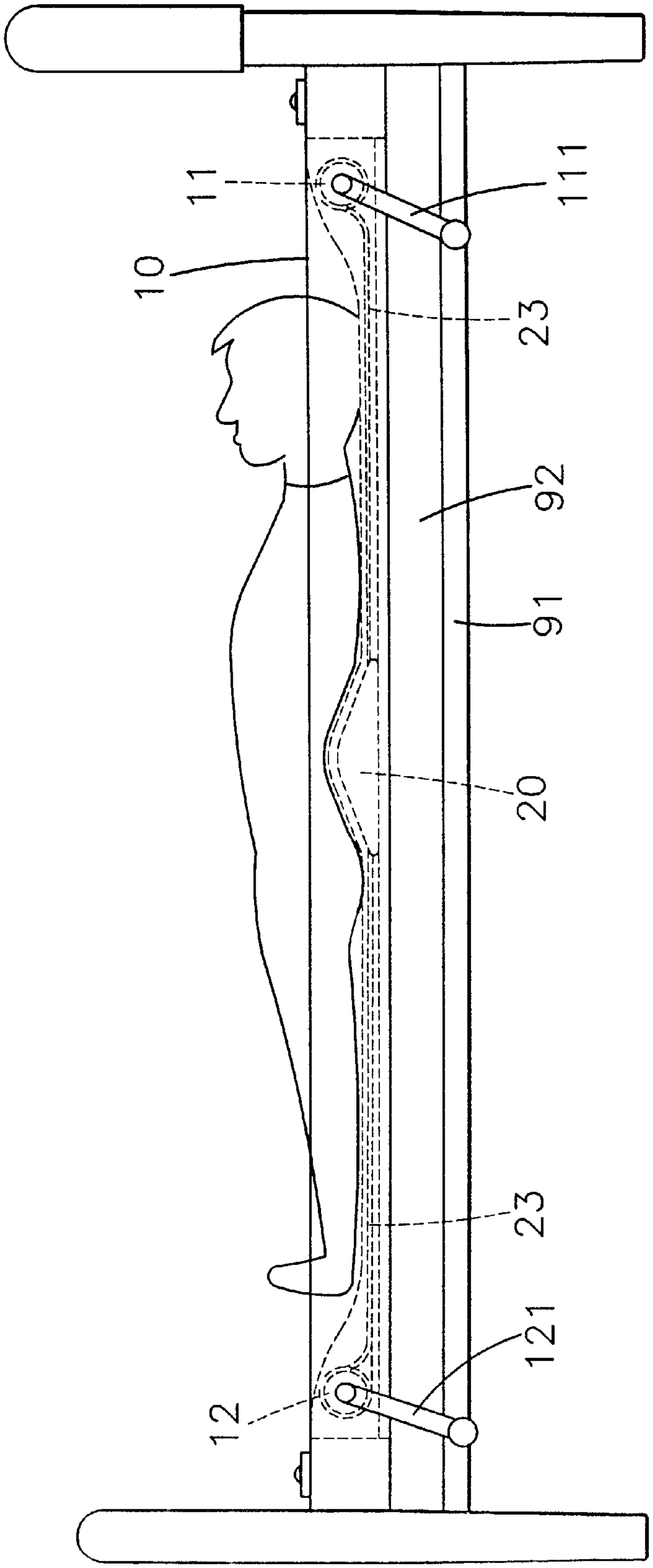
FIG. 5 is a side view showing the use of the present invention.
Figure 6:
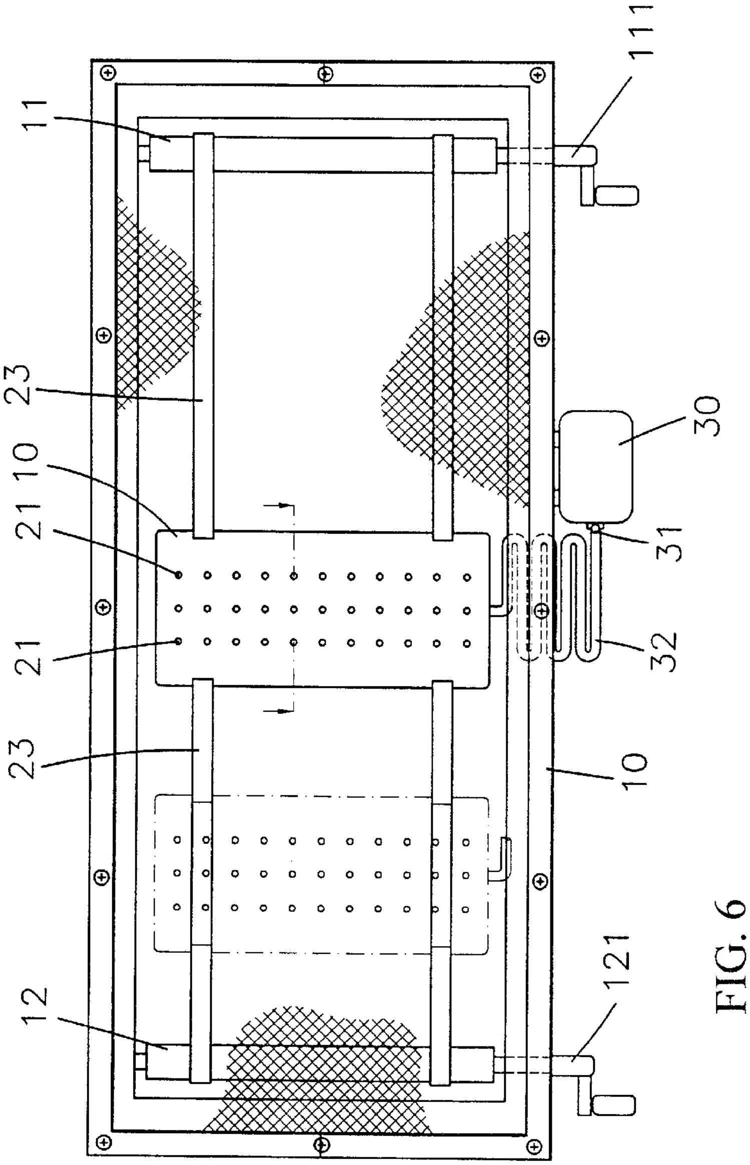
FIG. 6 is a top view of the present invention; and'
Figure 7:
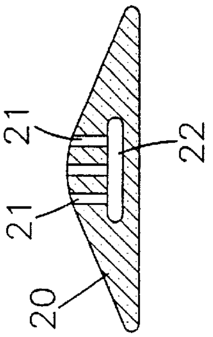
FIG. 7 is an enlarged sectional view of the ventilating device of the present invention.

Please refer to FIGS. 2 to 7. The ventilating bed cushion of the present invention includes a frame 10, a ventilating device 20, an air supplying device 30, an upper layer of air-permeable fabric 40 and a lower layer of waterproof fabric 50.

The frame 10 is pivotally connected with a front and a rear rollers 11, 12. A front and a rear cranks 111, 121 respectively outward extend from the front and rear rollers 11, 12.

The ventilating device 20 has a polished upper surface and a lower surface with low frictional coefficient. The upper surface is formed with multiple vents 21. The ventilating device 20 is formed with an inner air guide way 22. In addition, the ventilating device 20 is disposed with multiple connecting straps 23 for connecting with the front and rear rollers 11, 12.

A switch 31 (or a flow controlling valve) and a connecting tube 32 are disposed between the air supplying device 30 and the ventilating device 20 for supplying a predetermined amount of air to the ventilating device 20 or shutting off the air.

The soft upper air-permeable fabric 40 and the lower waterproof fabric 50 are both fixed on the frame 10 to enclose the ventilating device 20.

In operation, in the case that a ventilation operation is performed to the back of a user lying on the present invention, an operator can crank (or scroll) the front or the rear crank 11, 12. Accordingly, by means of the pulling of the connecting straps 23, the ventilating device 30 is moved to a desired position for supplying a predetermined amount of air to the surface of a user's body lying on the upper air-permeable fabric 40.

The present invention has the following functions and advantages:

1. Avoiding decubitus: With respect to physically defective users, such as an old-timer, a patient living in a hospital and a maimed person, a specific portion of the body can be forcedly ventilated so as to avoid decubitus caused by long term of poor ventilation of the skin.
2. Steaming and massaging treatment effect: The air supplying device can provide an air flow at a normal temperature. Moreover, the air supplying device can provide hot wind or steam instead of the air for thermally treating a specific portion of the patient's body such as the waist. Furthermore, the air supplying device can be used in cooperation with specific herbal medicine to achieve a herbal steaming treatment effect. Also, when moving the air supplying device, a massaging effect is achieved for the patient's back.
3. Wide application range: The present invention is applicable to a clinic bed of a hospital, a domestic bed and even a spring bed cushion with sufficient height. The present invention is only rested on the existent bed without changing the structure of the bed.
4. Simple operation: The cranks are manually operable to move the air supplying device. Therefore, a relative or a medical guardian taking care of the patient can easily operate the present invention.
5. Simple structure: The present invention is composed of a frame, a ventilating device, an air supplying device, an upper layer of air-permeable fabric and a lower layer of waterproof fabric so that the components of the present invention are simple.
6. Low manufacturing cost: The present invention is manufactured at low cost so that the patient can easily afford the present invention.

What is claimed is:

1. Ventilating bed cushion comprising:

a frame on which a front and a rear rollers are pivotally disposed, a front and a rear cranks respectively outward extending from the front and rear rollers;

a ventilating device having a polished upper surface and a lower surface, the upper surface being formed with multiple vents, the ventilating device being formed with an inner air guide way, the ventilating device being further disposed with multiple connecting members for connecting with the front and rear rollers;

an air supplying device, a switch and a connecting tube being disposed between the air supplying device and the ventilating device for supplying a predetermined amount of air to the ventilating device or shutting off the air; and an upper layer of fabric and a lower layer of fabric both fixed on the frame to enclose the ventilating device.

2. Ventilating bed cushion as claimed in claim 1, wherein the air supplying device can supply any of air at normal temperature, hot air, hot steam and herbal steam.

3. Ventilating bed cushion as claimed in claim 1, wherein the upper layer of fabric is an air-permeable fabric and the lower layer of fabric is a waterproof fabric.

* * * * *